United States Patent
Sigl et al.

(10) Patent No.: US 8,134,030 B2
(45) Date of Patent: Mar. 13, 2012

(54) PROCESS FOR PREPARING A PRIMARY AMINE WITH A TERTIARY ALPHA CARBON ATOM BY REACTING A TERTIARY ALCOHOL WITH AMMONIA

(75) Inventors: Marcus Sigl, Mannheim (DE); Thomas Heidemann, Viernheim (DE)

(73) Assignee: BASF SE, Ludwigshafen (DE)

( * ) Notice: Subject to any disclaimer, the term of this patent is extended or adjusted under 35 U.S.C. 154(b) by 119 days.

(21) Appl. No.: 12/739,572

(22) PCT Filed: Oct. 14, 2008

(86) PCT No.: PCT/EP2008/063787
§ 371 (c)(1),
(2), (4) Date: Apr. 23, 2010

(87) PCT Pub. No.: WO2009/053275
PCT Pub. Date: Apr. 30, 2009

(65) Prior Publication Data
US 2011/0009671 A1    Jan. 13, 2011

(30) Foreign Application Priority Data

Oct. 24, 2007 (EP) .................................... 07119205
Sep. 2, 2008 (EP) .................................... 08163456

(51) Int. Cl.
*C07C 209/16* (2006.01)
(52) U.S. Cl. ........ 564/478; 564/401; 564/402; 564/445; 564/479
(58) Field of Classification Search .................. 564/478, 564/479, 401, 402, 445
See application file for complete search history.

(56) References Cited

U.S. PATENT DOCUMENTS

| | | | |
|---|---|---|---|
| 1,875,747 A | | 9/1932 | Martin et al. |
| 2,012,333 A | * | 8/1935 | Ransom ........................ 564/479 |
| 3,384,667 A | | 5/1968 | Hamilton |
| 4,205,012 A | | 5/1980 | Parker |
| 4,370,503 A | | 1/1983 | Brake |
| 5,780,680 A | | 7/1998 | Karsten et al. |
| 6,143,934 A | | 11/2000 | Dingerdisseni et al. |
| 7,642,383 B2 | | 1/2010 | Heidemann et al. |

FOREIGN PATENT DOCUMENTS

| | | |
|---|---|---|
| DE | A-1 543 731 | 9/1969 |
| DE | B1-22 36040 | 11/1973 |
| DE | A-108 275 | 9/1974 |
| DE | A-149 213 | 7/1981 |
| DE | A1-197 23 949 | 12/1998 |
| EP | A1-50 870 | 5/1982 |
| EP | A-62 428 | 10/1982 |
| EP | A-64 380 | 11/1982 |
| EP | A-0118 193 | 9/1984 |
| EP | A-180 983 | 4/1986 |
| EP | A-324 267 | 7/1989 |
| JP | 4139156 | 5/1992 |
| JP | 8 157 428 | 6/1996 |
| JP | 2873068 | 1/1999 |
| WO | WO 97/07088 | 2/1997 |
| WO | WO-A-98/55228 | 12/1998 |
| WO | WO 2007/036478 | 4/2007 |

OTHER PUBLICATIONS

U.S. Appl. No. 12/601,653, filed Nov. 24, 2009, Sigl et al.
Srinivas N et al: Shape-Selective Synthesis of Collidines over Modified Zeolites:—Journal of Catalysis, Academic Press, Duluth, MN, US, vol. 208, No. 2, Jun. 10, 2002, pp. 332-338.

* cited by examiner

*Primary Examiner* — Brian J Davis
(74) *Attorney, Agent, or Firm* — Connolly Bove Lodge & Hutz LLP

(57) ABSTRACT

A process for preparing a primary amine with a tertiary alpha-carbon atom by reacting a tertiary alcohol with ammonia in the presence of a heterogeneous catalyst, by performing the reaction in the presence of a non-microporous, non-zeolitic aluminosilicate as a catalyst, where the aluminosilicate has a molar Al/Si ratio in the range from 0.1 to 30.

25 Claims, No Drawings

PROCESS FOR PREPARING A PRIMARY AMINE WITH A TERTIARY ALPHA CARBON ATOM BY REACTING A TERTIARY ALCOHOL WITH AMMONIA

This application is a National Phase filing under 35 U.S.C. §371 of PCT/EP2008/063787 filed Oct. 14, 2008, which claims priority to Patent Application No. 07119205.8, filed in Europe on Oct. 24, 2007 and Patent Application No. 08163456.0, filed in Europe on Sep. 2, 2008.

The present invention relates to a process for preparing a primary amine with a tertiary alpha-carbon atom by reacting a tertiary alcohol with ammonia in the presence of a heterogeneous catalyst.

Primary amines with tertiary alpha-carbon atoms find various uses as chemical intermediates.

For example, 1-adamantylamine, after it has been converted to 1-adamantyltrimethyl-ammonium hydroxide, can be used as a template for the hydrothermal synthesis of chabazite.

In addition, for example, tert-butylamine, after it has been converted to N-tert-butyl-2-benzothiazylsulfenamide, can be used as a process chemical for rubber production.

The reactants required for the process according to the invention, the appropriate tertiary alcohols, are commercially available.

For example, tert-butanol, which is required for the preparation of tert-butylamine, is obtained preferably from isobutenic hydrocarbon streams. For this purpose, technical C4 fractions are reacted with water over acidic catalysts, preferably 65% sulfuric acid. In addition, tert-butanol is also obtained as a coproduct in the preparation of propylene oxide.

Industrial processes for preparing a primary amine with a tertiary alpha-carbon atom by converting a tertiary alcohol are based on the Ritter reaction (cf. Römpp, Lexikon Chemie, 10th edition, Thieme Verlag, editors: J. Falbe, M. Regitz, volume 5 (1998), page 3836). In this process, tertiary alcohol is reacted with hydrocyanic acid in the presence of a stoichiometric amount of sulfuric acid. Subsequently, the mixture is neutralized with sodium hydroxide solution and, as well as the amine, sodium sulfate and sodium formate are formed as by-products.

The preparation of tert-butylamine from tert-butanol by the Ritter process is described, inter alia, in DE-B1-22 36040 (BASF AG) and EP-A1-50 870 (Degussa).

Clear disadvantages of the Ritter chemistry are the use of toxic hydrocyanic acid as the nitrogen source and a high occurrence of salt. There is accordingly a drive to replace hydrocyanic acid with ammonia as the nitrogen source.

Alcohols can be reacted with ammonia in principle in three ways:

Reductive amination over catalysts which can transfer hydrogen and comprise transition metals such as Ni, Co, Pd or Pt for this purpose.

Shape-selective amination over catalysts which comprise micropores, such as zeolites, molecular sieves or crystalline aluminosilicate.

Acidic amination over catalysts which have acidic sites, such as aluminum oxide or aluminosilicates (=mixed aluminum oxides and silicon oxides).

Processes for reductive amination are less suitable for preparing primary amines with a tertiary alpha-carbon atom, since, owing to the tertiary alpha-carbon atom, the formation of an imine intermediate is not possible.

For shape-selective amination, there is only one known document in which the reaction of tertiary alcohols is described (JP-A-041 39156, see below).

Processes for acidic amination are yet to be described for the reaction of tertiary alcohols with ammonia.

U.S. Pat. No. 3,384,667 (Mobil Oil Corp.) relates to the preparation of amines from aliphatic and aromatic alcohols, such as n-butanol and phenol (see the examples), and ammonia in the presence of particular crystalline aluminosilicate catalysts. The catalysts (zeolites) are microporous with a pore diameter in the range from 5 to 10 ångström (column 2, lines 3-14).

U.S. Pat. No. 4,205,012 (ICI Ltd.) describes the use of FU-1 zeolites as catalysts in the preparation of especially methylamines.

EP-A-180 983 (Air Products and Chemicals, Inc.) teaches the use of particular dealuminized zeolites, especially dealuminized H-mordenites, as catalysts in the preparation of especially ethylamines.

EP-A-324 267 (UOP) relates to the preparation of alkylamines from alcohols, especially the selective preparation of monomethylamine from methanol (page 2, lines 9-10), using non-zeolitic molecular sieves.

The non-zeolitic molecular sieves are characterized more accurately as crystalline structures which comprise at least the elements Al, Si and P (page 4, lines 55-57). Most structures are described explicitly as microporous (see, for example, page 8, lines 12-14; page 9, lines 43-44; page 11, lines 46-47; page 20, lines 37-38).

A process for preparing primary amines with a tertiary alpha-carbon atom from the corresponding alcohols is described in JP-A-041 39156 (Mitsui Toatsu Chem. Inc.). Here, the use of particular crystalline silicoaluminophosphate catalysts is taught. The catalysts are microporous.

The disadvantage of the microporous and crystalline catalysts described in the prior art is that the preparation thereof is generally inconvenient and costly, since organic template molecules have to be used in order to obtain the desired structures in the course of the hydrothermal syntheses, which have to be burnt out of the material after the crystallization.

It was an object of the present invention, while overcoming one or more disadvantages of the prior art, to discover an improved, economically viable process for preparing primary amines with a tertiary alpha-carbon atom.

Accordingly, a process has been found for preparing a primary amine with a tertiary alpha-carbon atom by reacting a tertiary alcohol with ammonia in the presence of a heterogeneous catalyst, which comprises performing the reaction in the presence of a non-microporous, non-zeolitic aluminosilicate as a catalyst, where the aluminosilicate has a molar Al/Si ratio in the range from 0.1 to 30.

More particularly, the process according to the invention is suitable for preparing a primary amine with a tertiary alpha-carbon atom of the formula RR'R"C—NH$_2$ by reacting a tertiary alcohol of the formula RR'R"C—OH where R, R' and R" are each organic radicals having in each case at least one carbon atom.

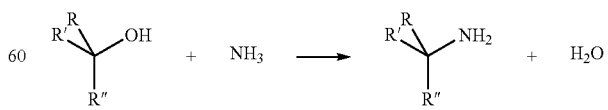

Very particular preference is given to using the process according to the invention to prepare tert-butylamine from 2-methyl-2-propanol, 1-adamantylamine from 1-adamantanol and 2-methyl-2-butylamine from 2-methyl-2-butanol.

The catalyst used in the process according to the invention is a non-microporous, non-zeolitic catalyst. The catalyst is amorphous (=non-crystalline).

In the present context, the term "non-microporous" is defined such that the catalyst has no pores having a diameter of less than 0.8 nm, preferably less than 1.2 nm, more preferably less than 1.5 nm and most preferably less than 2.0 nm.

Non-microporous aluminosilicate catalysts are used, for example, in industrial scale plants to prepare methylamines.

It has been recognized in accordance with the invention that non-microporous aluminosilicate catalysts can be used advantageously for the acidic amination to prepare primary amines with a tertiary alpha-carbon atom, for example of the general formula RR'R"C—$NH_2$, from the corresponding tertiary alcohols. Compared to shape-selective (zeolitic) amination catalysts, they have advantages in the preparation costs. Surprisingly, the process according to the invention affords the process product in very high selectivity. Conversion products such as secondary amines or by-products such as ethers, which are formed by condensation of two starting alcohols, are formed only in very small amounts.

The R, R' and R" radicals are each organic radicals which in each case have at least one carbon atom.

Preferably, R, R' and R" are each independently linear or branched alkyl radicals having in each case from 1 to 16 carbon atoms, preferably in each case from 1 to 6 carbon atoms, or cycloalkyl radicals having in each case from 5 to 7 carbon atoms. The R and R' and/or R" radicals may also be joined to form a 5- to 12-membered, preferably 6-membered, ring of carbon atoms.

Examples of the R, R' and R" radicals are (each independently): methyl, ethyl, n-propyl, isopropyl, n-butyl, isobutyl, n-pentyl, n-hexyl, n-heptyl, n-octyl, n-nonyl, n-decyl, cyclopentyl, cyclohexyl.

The process according to the invention can be performed as follows.

The amines are prepared by reacting ammonia with the appropriate tertiary alcohol under elevated pressure and at elevated temperature over the amorphous silica-alumina catalysts (mixed forms of aluminum oxide and silicon oxide). Optionally, the feed mixture may also comprise water and/or the amine to be prepared.

For the acidic amination in the process according to the invention, a fixed bed reactor system flowed through continuously is preferred. Suitable reactors are, for example, tubular reactors, tube bundle reactors, tray reactors, coil reactors or helical reactors. The conversion of the tertiary alcohols to the amines is exothermic. The temperature control can be carried out as usual with heat exchangers. The heat exchangers can be mounted in the reactor (internally) or outside the reactor (externally). Preference is given to performing the reaction in an adiabatic reactor system.

In order to use the catalyst in a fixed bed reactor system flowed through continuously, the catalyst is preferably used in the form of shaped bodies. The geometry of the shaped body is selected such that the pressure drop in the reactor is at a minimum.

The residence time in the reactor is preferably adjusted such that approximate thermodynamic equilibrium is achieved over the heterogeneous catalyst. This leads typically to catalyst hourly velocities in the range from 0.1 to 2.0 kg(tertiary alcohol)·kg(catalyst)$^{-1}$·h$^{-1}$, especially in the range from 0.2 to 1.5 kg(tertiary alcohol)·kg(catalyst)$^{-1}$·h$^{-1}$, very particularly in the range from 0.4 to 1.0 kg(tertiary alcohol)·kg(catalyst)$^{-1}$·h$^{-1}$.

The molar ammonia to tertiary alcohol ratio in the feed mixture is preferably in the range from 0.6 to 12, especially in the range from 0.8 to 4.0, very preferably in the range from 1 to 3, more preferably in the range from 1.1 to 2.5.

The reaction is carried out preferably at a temperature in the range from 220 to 500° C., in particular from 230 to 300° C., for example from 250 to 290° C.

In one process variant, the reaction is very preferably carried out at a temperature in the range from 300 to 475° C., more preferably from 325 to 450° C.

In a further preferred embodiment the reaction is carried out under isothermal conditions.

The absolute pressure of the reaction is preferably in the range from 5 to 400 bar, very preferably in the range from 10 to 250 bar and more preferably in the range from 20 to 100 bar.

The conversion of alcohol is preferably >10%, more preferably between 20% and 99.9%, especially between 30% and 99%.

The selectivity of the reaction to form the primary amine with a tertiary alpha-carbon atom as the process product (based on alcohol converted) is particularly >90%, very particularly >95%.

Unconverted ammonia and/or alcohol can be recycled after the amine has been removed and passed again over the catalyst. This recycle stream may also comprise water and/or amine, preferably in small amounts of less than 10% by weight, preferably less than 5% by weight.

Amorphous silica-alumina catalysts suitable for the process according to the invention, i.e. non-microporous, non-zeolitic aluminosilicates, where the aluminosilicate has a molar Al/Si ratio in the range from 0.1 to 30, can be selected, for example, from the catalysts described in the following documents which relate to the preparation of methylamines:

WO-A-2007/036478 (BASF AG) describes a shaped body comprising an aluminosilicate and aluminum oxide, where the shaped body has a molar Al/Si ratio in the range from 10 to 30 and an at least bimodal pore distribution for pores having a diameter of greater than 1 nm, where the volume of the pores of the shaped body having a diameter of greater than 10 nm corresponds to at least 40% of the total pore volume of the shaped body.

U.S. Pat. No. 1,875,747 (Martin et al.) discloses aluminosilicate catalysts. The aluminosilicate can be used as synthetic solid or in the form of alumina.

EP-A-64 380 (DuPont) describes a catalyst which is obtained by the treatment of an aluminosilicate with the hydroxide salts of sodium, of potassium, of lithium, of barium or of strontium, where the proportion of Na, K, Li, Ba or Sr is between 0.1 and 6% by weight.

DD-A-149 213 (VEB Leuna) discloses dehydrating catalysts which comprise active aluminum oxide, and a catalyst is described which is prepared on the basis of kaolin and pseudoboehmite, which, as well as aluminum oxide, comprises from 12 to 18% by weight of silicon dioxide, and whose total pore volume is greater than 0.5 ml/g, where the proportion of pores having a diameter less than 4 nm is at least 30% and that of pores having a diameter greater than 15 nm is at most 10%, and its particle size or wall thickness is less than 4 mm. The proportion of $SiO_2$ between 12 and 18% corresponds to a molar Al/Si ratio between 5.4 and 8.6.

EP-A-62 428 (=U.S. Pat. No. 4,370,503) (DuPont) describes a catalyst consisting of from 88 to 99% by weight of alumina and from 1 to 13% by weight of silica. The weight distributions of silica and alumina correspond to a molar Al/Si ratio of from 7.9 to 116.7. The catalyst is typically present in the form of a tablet having a diameter and/or length of from 3 to 13 mm. The pore volume of the tablet is between 0.2 and 0.8 ml/g, the BET surface area between 100 and 250 m$^2$/g.

DD-A-108 275 (Becker et al.) describes catalysts consisting of aluminum oxide and/or aluminosilicates, where the catalyst is used in the form of a hollow extrudate whose total diameter is from 3 to 10 mm and whose cavity diameter is from 1 to 5 mm, a total pore volume of at least 30% of pores having a diameter greater than 100 Å, a surface area of at least 130 m$^2$/g and an acidity of at most $2.0 \times 10^{-5}$ mol of $NH_3$/g.

DE-A-1 543 731 (Leonard) teaches catalysts, where the catalyst consists of a silica gel base on which active aluminum oxide and traces of metal salt mediators have been applied, and the catalyst is partly deactivated before use by a treatment with steam of 1-50 atmospheres. The catalyst comprises typically between 12 and 13% by weight of $Al_2O_3$. The steam treatment reduces the total surface area of the catalyst to $90\pm20$ m$^2$/g and adjusts the pore volume to $0.34\pm0.10$ ml/g and the pore diameter to $74\pm10$ Å.

Of particular industrial interest and therefore preferred are catalysts which have a long lifetime. This is achieved in the catalysts used in the process according to the invention firstly by virtue of the acidity being adjusted such that activation of the reactants by complex formation with the active center is possible, but the complexes are not so stable that coke and/or coke precursors form or deactivate the active centers. Secondly, the porosity is adjusted such that sufficient diffusion of the reactants and products from and to the active centers and of the reaction medium into and out of the pores of the catalyst is possible under the given reaction conditions. Such catalysts are described, for example, in WO-A-2007/036478 (BASF AG; see above).

A suitable catalyst is prepared preferably by a process which comprises the following steps:
(I) Preparing a mixture comprising an $SiO_2$ source, an $Al_2O_3$ source and a binder,
(II) Mixing and compacting the mixture,
(III) Shaping the compacted mixture to obtain a shaped body,
(IV) Calcining the shaped body.

For the preparation of the mixture in step (I), preference is given to using clays, and it is especially preferably possible to use sheet silicates from the kaolin group (see Ullman's Encylopedia of Industrial Chemistry, 6th edition, 2000 electronic edition, chapter 2 and Lehrbuch der Anorganischen Chemie [Textbook of Inorganic Chemistry], 91st-100th edition, 1985, pages 771-776). Very particular preference is given to using kaolinite.

The binders used for step (I) are preferably aluminum compounds which are converted to $\gamma$-$Al_2O_3$ to an extent of at least 80% in the final calcination step. They include aluminum hydroxide and/or aluminum oxide/hydroxide. The aluminum hydroxide used may be either the synthetic $Al(OH)_3$ or the natural hydrargillite [$\gamma$-$Al(OH)_3$]. The aluminum oxide/hydroxide [$\gamma$-$Al(O)OH$] used is preferably boehmite and/or pseudoboehmite. In a particular embodiment, a mixture of aluminum hydroxide and/or aluminum oxide/hydroxide and $\gamma$-$Al_2O_3$ is used as the precursor.

When naturally occurring minerals are used for the preparation of the catalyst, they may, as well as silicon and/or aluminum, also comprise the elements titanium, iron, sodium and/or potassium in traces. The proportion of these elements is preferably between 0.1 and 1.0% by weight for titanium, between 0.1 and 1.0% by weight for iron, between 0.1 and 5.0% by weight for potassium and between 0.1 and 5.0% by weight for sodium.

The mixture is homogenized in step (II) preferably in a kneader, pan grinder or extruder, for example for a period in the range from 10 to 180 minutes. On a smaller scale, the mixture is preferably kneaded. On the industrial, larger scale, homogenization is preferably effected by pan grinding. In the homogenization, preference is given to working at temperatures of from about 10° C. to 100° C. and under standard pressure or slight superatmospheric pressure. Homogenization is effected until a deformable plastic material has formed.

The shaping in step (III) is effected preferably by extrusion, tableting, briqueting or pelletizing. The shape of the shaped bodies produced for the process according to the invention can be selected as desired. In particular, shapes including spheres, oval shapes, extrudates or tablets are possible.

Preference is given to cylindrical shaped bodies having a diameter in the range from 0.5 to 20 mm, preferably in the range from 1 to 10 mm, where the length:diameter ratio is especially in the range from 0.5 to 20, preferably in the range from 1 to 10, more preferably in the range from 1.5 to 5.

In the context of the present invention, particular preference is given to performing the shaping by extrusion of the mixture obtained in step II.

The calcination in step (IV) is performed at temperatures in the range from preferably 350 to 750° C. and especially from 450 to 700° C.

The calcination can be effected under any suitable gas atmosphere, preference being given to air and/or lean air.

In addition, the calcination is preferably carried out in a muffle furnace, a rotary tube furnace and/or a belt calcination oven, where the calcination time is preferably 1 h or more, for example in the range from 1 to 24 h or in the range from 3 to 12 h. Accordingly, it is possible, for example, in the process according to the invention to calcine the shaped body once, twice or more than twice for at least 1 h each time, for example for in the range from 3 to 12 h each time, and the temperatures can remain the same or be changed continuously or discontinuously during a calcination step. When calcination is effected twice or more than twice, the calcination temperatures in the individual steps may be different or the same.

After the calcination step, the calcined material can, for example, be comminuted. Preference is given to obtaining granules or spall having a particle size in the range from 0.1 to 5 mm, especially from 0.5 to 2 mm.

The resulting shaped bodies have hardnesses which are preferably in the range from 2 to 200 N (newtons), more preferably in the range from 5 to 150 N and most preferably at least 10 N, for example in the range from 10 to 100 N.

In the context of the present invention, the above-described hardness was determined on an apparatus from Zwick, BZ2.5/TS1S type, with an initial force of 0.5 N, an advance rate of the initial force of 10 mm/min and a subsequent testing rate of 1.6 mm/min. The instrument had a fixed turntable and a freely mobile plunger with incorporated blade of thickness 0.3 mm. The mobile plunger with the blade was connected to a load cell to record the force and moved during the measurement against the fixed turntable on which the shaped catalyst body to be studied lay. The test instrument was controlled by means of a computer which registered and evaluated the test results. The values achieved constitute the mean value from the measurements for at least 10 shaped catalyst bodies in each case.

The catalyst preferably has a molar Al/Si ratio in the range from 0.1 to 30, preferably from 1 to 25, especially preferably from 2 to 20. The data for the molar Al/Si ratio in the shaped body are based on the total content of Al and Si.

The specific surface area of the catalyst, determined to DIN 66131 (BET), is preferably at least 50 m$^2$/g and especially preferably at least 100 m$^2$/g. For example, the specific surface area is in the range from 100 to 250 m$^2$/g and especially in the range from 120 to 200 m$^2$/g.

The pore volume of the catalyst, determined to DIN 66134 (Hg porosimetry), is preferably at least 0.4 ml/g, more preferably at least 0.6 ml/g. For example, the pore volume is in the range from 0.4 to 1.5 ml/g and especially in the range from 0.6 to 1.0 ml/g.

In a preferred embodiment, the catalyst comprises traces of titanium, iron, sodium and/or potassium, in each case in ionic form. The proportion of these elements is in the range from $\geq 0.01$ to $\leq 0.35\%$ by weight, preferably $\geq 0.05$ to $\leq 0.15\%$ by weight, for titanium, in the range from $\geq 0.01$ to $\leq 0.35\%$ by weight, preferably $\geq 0.02$ to $\leq 0.10\%$ by weight, for iron, in the range from $\geq 0.01$ to $\leq 1.75\%$ by weight, preferably $\geq 0.10$ to $\leq 0.70\%$ by weight, for potassium and in the range from $\geq 0.01$ to $\leq 1.75\%$ by weight, preferably $\geq 0.10$ to $\leq 0.70\%$ by weight, for sodium, based in each case on the shaped body weight.

More preferably, the catalyst does not comprise any phosphorus in any oxidation state.

Regeneration of the Catalyst

In a further embodiment of the process according to the invention, the catalyst, after use, irrespective of its shape, for example after decrease in the activity and/or in the selectivity, is regenerated via a process in which the regeneration is effected by controlled burning-off (at, for example, a temperature in the range from 350 to 650° C.) of the deposits responsible for the deactivation. Preference is given to working in an inert gas atmosphere which comprises exactly defined amounts of oxygen or oxygen-providing substances. Such a regeneration process is described, inter alia, in WO-A-98/55228 and DE-A1-197 23 949, and more particularly for catalysts for preparing methylamines in JP-08 157 428 and EP-A-0118 193.

After the regeneration, the activity and/or the selectivity of the catalyst, compared to the state immediately before the regeneration, are increased.

The catalyst which is used in the process according to the invention and is to be regenerated is heated either in the reaction apparatus (reactor) or in an external oven, in an atmosphere which comprises from 0.1 to about 20 parts by volume of oxygen-providing substances, more preferably from 0.1 to 20 parts by volume of oxygen, to a temperature in the range from 350° C. to 800° C., preferably from 400° C. to 650° C. and especially from 425° C. to 500° C. The heating is carried out preferably with a heating rate of from 0.1° C./min to 20° C./min, preferably from 0.3° C./min to 15° C./min and especially from 0.5° C./min to 10° C./min. The heating is carried out preferably under an inert atmosphere.

During the regeneration, the catalyst is heated up to a temperature at which the usually organic deposits present there begin to decompose, while the temperature is simultaneously controlled via the oxygen content and thus does not rise such that there is damage to the catalyst structure or to the reactor. The slow increase in the temperature and the residence at low temperature as a result of establishment of the appropriate oxygen content and of the appropriate heating output is a significant step toward prevention of local overheating of the catalyst in the case of high organic loadings of the catalyst to be regenerated. The gas loading of the oxygen-comprising regeneration gas expressed as GHSV (=gas hourly space velocity) is preferably more than 50 standard liters per liter of catalyst and hour (=l(STP)/l(cat)h), more preferably more than 100 l(STP)/l(cat)h and especially preferably in the range between 150 and 1000 l(STP)/l(cat)h.

(l STP=standard liters=volume converted to standard temperature and pressure conditions).

When the temperature of the offgas stream at the reactor outlet falls to the temperature at the reactor inlet in spite of rising amounts of oxygen or oxygen-providing substances in the gas stream and/or when the concentration of oxygen in the reaction effluent rises to the starting value, the burnoff of the organic deposits has ended. The duration of the treatment is preferably in each case from 1 to 72 h, preferably from about 2 to about 48 h and especially from about 3 to about 24 hours.

The subsequent cooling of the catalyst thus regenerated is preferably carried out in such a way that the cooling is not effected too rapidly, since the mechanical integrity of the catalyst can otherwise be adversely affected. The cooling is preferably carried out under an inert atmosphere.

After performance of regeneration by calcination, it may be necessary to subject the catalyst, as described above, to a rinse with water and/or dilute acids, for example hydrochloric acid, in order to remove any inorganic loading of the catalyst which remains as a result of contamination of the reactants (alkali traces, etc.). Subsequently, another drying and/or another calcination of the catalyst can be carried out.

In a further embodiment of the process according to the invention, the at least partly deactivated catalyst, before the heating in the regeneration procedure, is washed with a solvent in the reactor for the reaction or in an external reactor in order to remove product of value still adhering. In this case, the wash is carried out such that the products of value adhering on the catalyst can be removed therefrom in each case, but temperature and pressure are not selected at such a high level that the usually organic deposits are likewise removed. Preference is given to merely rinsing the catalyst with a suitable solvent. For this washing operation, all solvents in which the particular reaction product dissolves readily are therefore suitable. The amount of solvent used and the duration of the washing operation are not critical. The washing operation can be repeated several times and can be carried out at elevated temperature. When $CO_2$ is used as the solvent, supercritical pressure is preferred; otherwise, the washing operation can be effected under standard pressure or elevated or supercritical pressure. Once the washing operation has ended, the catalyst is generally dried. Even though the drying operation is generally uncritical, the drying temperature should not too greatly exceed the boiling point of the solvent used for washing, in order to prevent sudden evaporation of the solvent in the pores, since this can lead to damage to the catalyst.

A preferred embodiment of the preparation process consists in not interrupting the process according to the invention for synthesizing the primary amines in the case of continuous performance in the regeneration of the catalyst used in accordance with the invention, in order thus to increase the process throughput. This can be achieved by the use of at least two reactors connected in parallel, which can be operated in alternation.

The catalyst regeneration can be carried out by disconnecting at least one of the reactors connected in parallel from the particular reaction stage and regenerating the catalyst present in this reactor, in which case at least one reactor is always available for converting the reactants in each stage in the course of the continuous process.

EXAMPLES

For the reactions which follow, an amorphous silica-alumina catalyst, in the form of 1.0 to 1.6 mm spall, with a molar Al/Si ratio=25 was used, which additionally comprised 0.04% by weight of Fe, 0.32% by weight of K and 0.09% by weight of Ti.

Mercury porosimetry (DIN 66134) was used to determine a pore volume of 0.56 ml/g and a mean pore diameter of 0.01 μm. The BET surface area (DIN 66131) was 210 m²/g.

1)

The reactions were effected in a stirred autoclave, in which alcohol and catalyst were initially charged and then ammonia was injected. The reaction mixture was heated to the desired temperature under autogenous pressure and cooled and decompressed to atmospheric pressure after a reaction time of 12 h. The autoclave contents were taken up in methanol and analyzed in a gas chromatograph. The composition of the effluent is reported in FID area %.

| Reaction conditions | | | | | | |
|---|---|---|---|---|---|---|
| Run | R—OH | m(R—OH) | m(NH3) | m(cat.) | T | p |
| 1 | tert-BuOH | 24 g | 51 g | 4 g | 325° C. | 390 bar |
| 2 | adamantanol | 25 g | 62 g | 20 g | 329° C. | 450 bar |

| Analysis of reaction effluent, FID area % | | |
|---|---|---|
| Run | R-OH | R-NH2 |
| 1 (R = tert-butyl) | 86.3% | 12.0% |
| 2 (R = 1-adamantyl) | 79.2% | 20.4% |

2)

In a tubular reactor (internal diameter 6 mm), mixtures of ammonia and t-BuOH in a molar ratio of 3-10:1 were converted under isothermal conditions at temperatures of 240-290° C. and pressures of 35-100 bar.

Exact reaction conditions, t-BuOH conversions achieved and t-butylamine selectivities are summarized in the table below.

| | | | | | | | |
|---|---|---|---|---|---|---|---|
| Amount of catalyst | g | 10 | 10 | 10 | 10 | 10 | 10 |
| nNH3:nC4 | mol:mol | 10 | 3 | 10 | 10 | 10 | 10 |
| t-BuOH metering rate | g/h | 6 | 6 | 6 | 3 | 6 | 6 |
| NH3 metering rate | g/h | 14 | 4 | 14 | 7 | 14 | 14 |
| Cat. hourly space velocity | g C4/g cat./h | 0.6 | 0.6 | 0.6 | 0.3 | 0.6 | 0.6 |
| p | bar | 100 | 100 | 100 | 100 | 100 | 35 |
| T | ° C. | 260 | 260 | 240 | 260 | 290 | 260 |
| t-BuOH conversion | % | 20 | 25 | 12 | 25 | 30 | 40 |
| t-BuNH2 selectivity | % | 98 | 70 | 99 | 90 | 70 | 70 |

The results illustrate that, with t-BuOH in straight pass, higher conversions can be run than in the case of isobutene/$NH_3$ conversions over a zeolite catalyst. In addition, high-pressure plants are not required.

The invention claimed is:

1. A process for preparing a primary amine with a tertiary alpha-carbon atom by reacting a tertiary alcohol with ammonia in the presence of a heterogeneous catalyst, which comprises performing the reaction in the presence of a non-microporous, non-zeolitic aluminosilicate as a catalyst, where the aluminosilicate has a molar Al/Si ratio in the range from 0.1 to 30.

2. The process according to claim 1, wherein the primary amine is represented by the formula RR'R"C—$NH_2$; wherein the tertiary alcohol is represented by the formula RR'R"C—OH; and wherein R, R' and R" are each organic radicals having in each case at least one carbon atom.

3. The process according to claim 1, wherein the tertiary alcohol is 2-methyl-2-propanol, 2-methyl-2-butanol or 1-adamantanol.

4. The process according to claim 1, wherein the catalyst has a molar Al/Si ratio in the range from 1 to 25.

5. The process according to claim 1, wherein the catalyst has a pore volume greater than 0.3 ml/g.

6. The process according to claim 1, wherein the catalyst has a pore volume in the range from 0.4 to 1.5 ml/g.

7. The process according to claim 1, wherein the catalyst has a BET surface area of $\geq 50$ m$^2$/g.

8. The process according to claim 1, wherein the catalyst has a BET surface area in the range from 100 to 250 m$^2$/g.

9. The process according to claim 1, wherein the catalyst further comprises in the range from 0.01 to 1.75% by weight of sodium, from 0.01 to 1.75% by weight of potassium, from 0.01 to 0.35% by weight of titanium and/or from 0.01 to 0.35% by weight of iron, in each case in ionic form and based in each case on the total weight of the catalyst.

10. The process according to claim 1, wherein the catalyst does not comprise any phosphorus.

11. The process according to claim 1, wherein the catalyst is used in the form of a shaped body with a length to diameter ratio of $\geq 0.5$.

12. The process according to claim 1, wherein the catalyst is used in the form of a shaped body with a cutting hardness of $\geq 10$ newtons (N).

13. The process according to claim 1, wherein kaolin is used as the silicon source for the preparation of the catalyst.

14. The process according to claim 1, wherein the catalyst comprises aluminum oxide in the form of gamma-$Al_2O_3$.

15. The process according to claim 14, wherein aluminum hydroxide and/or aluminum oxide/hydroxide (boehmite or pseudoboehmite) is used as a precursor for the gamma-$Al_2O_3$ in the catalyst.

16. The process according to claim 1, wherein the preparation of the catalyst includes an extrusion step or a tableting step.

17. The process according to claim 1, wherein the preparation of the catalysts includes a calcination step.

18. The process according to claim 17, wherein the calcination step is carried out at a temperature in the range from 350 to 750° C. and for a duration in the range from 1 to 24 h.

19. The process according to claim 1, wherein the ammonia and tertiary alcohol reactants are used in a molar ammonia to tertiary alcohol ratio in the range from 0.6 to 12.

20. The process according to claim 1, wherein the ammonia and tertiary alcohol reactants are used in a molar ammonia to tertiary alcohol ratio in the range from 1 to 3.

21. The process according to claim 1, wherein the reaction is performed at a temperature in the range from 220 to 500° C.

22. The process according to claim 1, wherein the reaction is carried out at an absolute pressure in the range from 5 to 400 bar.

23. The process according to claim 1, wherein the reaction is performed at an absolute pressure in the range from 10 to 250 bar.

24. The process according to claim 1, wherein a catalyst hourly velocity is in the range from 0.1 to 2.0 kg of the tertiary alcohol per kg of the catalyst per hour.

25. The process according to claim 1, wherein the catalyst used is regenerated by controlled burning-off of the deposits responsible for the deactivation.

* * * * *